US012685711B2

(12) United States Patent
Opara

(10) Patent No.: US 12,685,711 B2
(45) Date of Patent: Jul. 21, 2026

(54) FORMULATIONS FOR PANCREATIC ISLET ENCAPSULATION

(71) Applicant: Wake Forest University Health Sciences, Winston-Salem, NC (US)

(72) Inventor: Emmanuel C. Opara, Durham, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 810 days.

(21) Appl. No.: 17/267,661

(22) PCT Filed: Aug. 13, 2019

(86) PCT No.: PCT/US2019/046278
§ 371 (c)(1),
(2) Date: Feb. 10, 2021

(87) PCT Pub. No.: WO2020/036918
PCT Pub. Date: Feb. 20, 2020

(65) Prior Publication Data
US 2021/0196646 A1 Jul. 1, 2021

Related U.S. Application Data

(60) Provisional application No. 62/764,695, filed on Aug. 15, 2018.

(51) Int. Cl.
*A61K 35/39* (2015.01)
*A61K 9/50* (2006.01)
*C12N 11/04* (2006.01)
*C12N 11/10* (2006.01)

(52) U.S. Cl.
CPC ............ *A61K 9/5036* (2013.01); *A61K 35/39* (2013.01); *C12N 11/04* (2013.01); *C12N 11/10* (2013.01)

(58) Field of Classification Search
CPC ...... A61K 9/5036; A61K 35/39; C12N 11/04; C12N 11/10
See application file for complete search history.

(56) References Cited

U.S. PATENT DOCUMENTS

| | | | |
|---|---|---|---|
| 4,391,909 A | 7/1983 | Lim | |
| 6,365,385 B1 | 4/2002 | Opara | |
| 6,783,964 B2 | 8/2004 | Opara | |
| 7,759,111 B2 | 7/2010 | Lee et al. | |
| 2003/0170215 A1* | 9/2003 | Tsang | C12N 5/0676 |
| | | | 435/366 |
| 2008/0171704 A1* | 7/2008 | Vinik | A61P 3/00 |
| | | | 514/6.9 |
| 2008/0199914 A1* | 8/2008 | Skjak-Braek | C08B 37/0072 |
| | | | 435/178 |
| 2009/0010983 A1* | 1/2009 | Melvik | A61L 27/52 |
| | | | 435/402 |
| 2011/0177593 A1* | 7/2011 | Funaki | C12N 5/0068 |
| | | | 435/375 |
| 2014/0017304 A1* | 1/2014 | Bosmans | A61K 35/407 |
| | | | 264/4.1 |
| 2014/0322342 A1* | 10/2014 | Opara | A61K 47/42 |
| | | | 424/490 |
| 2016/0051726 A1* | 2/2016 | Flynn | A61L 27/26 |
| | | | 428/221 |
| 2021/0145759 A1* | 5/2021 | Barney | A61K 35/30 |

OTHER PUBLICATIONS

Stabler et al (Ann. N.Y. Acad. Sci. 961: 130-133 (2002), https://doi.org/10.1111/j.1749-6632.2002.tb03065.x, Jan. 24, 2006) (Year: 2006).*

Llacua et al (J Biomed Mater Res Part A 2016:104A:1788-1796., DOI: 10.1002/jbm.a.35706, Mar. 22, 2016) (Year: 2016).*

Mørch et al (Biomacromolecules 2006, 7, 1471-1480, https://doi.org/10.1021/bm060010d, Apr. 12, 2006). (Year: 2006).*

Safley et al (Journal of Surgical Research vol. 179, Issue 2, Feb. 2013, pp. 264-265, Doi: 10.1016/j.jss.2012.10.506) (Year: 2013).*

Matyash et al (Tissue Engineering: Part A vol. 18, Nos. 1 and 2, 2012, DOI: 10.1089/ten.tea.2011.0097) (Year: 2012).*

Alberts, Bruce, et al., "The extracellular matrix of animals", Molecular Biology of the Cell. 4th edition. New York: Garland Science, 2002, 32 pp.

Augst, Alexander D., et al., "Alginate Hydrogels as Biomaterials", Macromol. Biosci., 6(8), 2006, 623-633.

Badylak, Stephen F., et al., "Extracellular matrix as a biological scaffold material: Structure and function", Acta Biomaterialia, 5(1), 2009, 1-13.

Barralet, J. E., et al., "Comparison of bone marrow cell growth on 2D and 3D alginate hydrogels", Journal of Materials Science: Materials in Medicine, 16(6), 2005, 515-519.

Calafiore, Riccardo, et al., "Alginate/poly-L-ornithine microcapsules for pancreatic islet cell immunoprotection", Cell Encapsulation Technology and Therapeutics; Springer, Boston, MA, 1999, 138-150.

Darrabie, Marcus D., et al., "Characteristics of Poly-I-Ornithine-coated alginate microcapsules", Biomaterials, 26(34), 2005, 6846-6852.

Darrabie, Marcus D., et al., "Effect of alginate composition and gelling cation on microbead swelling", Journal of microencapsulation, 23(1), 2006, 613-621.

(Continued)

*Primary Examiner* — Peter Paras, Jr.
*Assistant Examiner* — Khoa Nhat Tran
(74) *Attorney, Agent, or Firm* — Myers Bigel, P.A.

(57) ABSTRACT

Provided herein according to embodiments of the present invention is a microcapsule comprising: (a) one or more live mammalian pancreatic islet cells; and (b) an alginate composition encapsulating said islet cells, wherein said alginate composition comprises extracellular matrix proteins solubilized or suspended therein. Compositions comprising a plurality of the microcapsules and the use thereof in treating type I diabetes are also provided.

15 Claims, 2 Drawing Sheets

(56) References Cited

OTHER PUBLICATIONS

De Vos, Paul , et al., "Alginate-based microcapsules for immunoisolation of pancreatic islets", Biomaterials, 27(32), 2006, 5603-5617.

De Vos, Paul , et al., "Improved biocompatibility but limited graft survival after purification of alginate for microencapsulation of pancreatic islets", Diabetologia, 40(3), 1997, 262-270.

Discher, Dennis E., et al., "Tissue Cells Feel and Respond to the Stiffness of Their Substrate", Science, 310(5751, 2005, 1139-1143.

Elliott, Robert B., et al., "Live encapsulated porcine islets from a type 1 diabetic patient 9.5 yrs after xenotransplantation", Xenotransplantation 14(2), 2007, 157-161.

Engler, Adam J., et al., "Matrix Elasticity Directs Stem Cell Lineage Specification", Cell, 126(4), 2006, 677-689.

Evans, Nicholas D., et al., "Substrate stiffness affects early differentiation events in embryonic stem cells", European Cells and Material, 18(1), 2009, 1-14.

Farney, Alan C., "Evolution of Islet Transplantation for the Last 30 Years", Pancreas 45(1), 2016, 8-20.

Fraker, Christopher A., "The Role of Oxygen During In Vitro Culture and Immunoisolation of Islets of Langerhans", Doctoral Dissertation, University of Miami, 2011, 1-271.

Frantz, Christian , et al., "The extracellular matrix at a glance", J Cell Sci, 123(24), 2010, 4195-4200.

Freytes, Donald O., et al., "Preparation and rheological characterization of a gel form of the porcine urinary bladder matrix", Biomaterials, 29(11), 2008, 1630-1637.

Gasperini, Luca, et al., "Natural polymers for the microencapsulation of cells", Journal of the Royal Society Interface, 11(100)., 2014, 1-19.

Gilbert, P. M. , et al., "Substrate Elasticity Regulates Skeletal Muscle Stem Cell Self-Renewal in Culture", Science, 329(5995), 2010, 1078-1081.

Ho, Steve S., et al., "Increased Survival and Function of Mesenchymal Stem Cell Spheroids Entrapped in Instructive Alginate Hydrogels", Stem Cells Translational Medicine , 5(6), 2016, 773-781.

Hunt, Nicola C., et al., "3D culture of human pluripotent stem cells in RGD-alginate hydrogel improves retinal tissue development", Acta Biomaterialia, 49, 2017, 329-343.

Ibarra, Veronica , et al., "Evaluation of the tissue response to alginate encapsulated islets in an omentum pouch model", J Biomed Mater Res A, 104(7), 2016, 1581-1590.

Jansson, L. , et al., "Stimulation by glucose of the blood flow to the pancreatic islets of the rat", Diabetologia, 25, 1983, 45-50.

Jiang, K. , et al., "3-D physiomimetic extracellular matrix hydrogels provide a supportive microenvironment for rodent and human islet culture", Biomaterials, 198, 2019, 37-48.

Lee, Bo Ram , et al., "In situ formation and collagen-alginate composite encapsulation of pancreatic islet spheroids", Biomaterials, 33(3), 2012, 837-845.

Lifson, Nathan , et al., "Blood flow to the rabbit pancreas with special reference to the islets of langerhans", Gastroenterology, 79(3), 1980, 466-473.

Lim, Franklin , et al., "Microencapsulated islets as bioartificial endocrine pancreas", Science 210(4472), 1980, 908-910.

Llacua, Alberto , et al., "Extracellular matrix components supporting human islet function in alginate-based immunoprotective microcapsules for treatment of diabetes", Journal of biomedical materials research Part A, 104(7), 2016, 1788-1796.

Lopez, J. I. , et al., "Biomechanical regulation of cell orientation and fate", Oncogene, 27(55), 2008, 6981-6993.

Maia, F. Raquel, et al., "Effect of Cell Density on Mesenchymal Stem Cells Aggregation in RGD-Alginate 3D Matrices under Osteoinductive Conditions", Macromolecular bioscience, 14(6), 2014, 759-771.

Mcquilling, J. P. , et al., "New Alginate Microcapsule System for Angiogenic Protein Delivery and Immunoisolation of Islets for Transplantation in the Rat Omentum Pouch", Transplantation Proceedings, 43(9), 2011, 3262-3264.

Nicodemus, Garret D., et al., "Cell Encapsulation in Biodegradable Hydrogels for Tissue Engineering Applications", Tissue Engineering Part B: Reviews, 14(2), 2008, 149-165.

Opara, Emmanuel C., et al., "Microencapsulation of Pancreatic Islets for Use in a Bioartificial Pancreas", Basu J., Ludlow J. (eds) Organ Regeneration. Methods in Molecular Biology (Methods and Protocols), vol. 1001. Humana Press, Totowa, NJ., 2013, 261-266.

Pathak, Amit , et al., "Independent regulation of tumor cell migration by matrix stiffness and confinement", PNAS, 109(26, 2012, 10334-10339.

Riopel, Matthew , et al., "Collagen matrix support of pancreatic islet survival and function", Front Biosci, 19(1), 2014, 77-90.

Rowley, Jon A., et al., "Alginate hydrogels as synthetic extracellular matrix materials", Biomaterials, 20(1), 1999, 45-53.

Rowley, Jon A., et al., "Alginate type and RGD density control myoblast phenotype", Journal of Biomedical Materials Research, 60(2), 2002, 217-223.

Saldin, Lindsey T., et al., "Extracellular matrix hydrogels from decellularized tissues: Structure and function", Acta Biomaterialia, 49, 2017, 1-15.

Skardal, Aleksander , et al., "A hydrogel bioink toolkit for mimicking native tissue biochemical and mechanical properties in bioprinted tissue constructs", Acta Biomaterialia, 25, 2015, 24-34.

Tendulkar, Sameer , et al., "A Scalable Microfluidic Device for the Mass Production of Microencapsulated Islets", Transplantation Proceedings, 43(9), 2011, 3184-3187.

Vaithilingam, Vijayaganapathy , et al., "Islet Transplantation and Encapsulation: An Update on Recent Developments", Rev Diabet Stud., 8(1), 2011, 51-67.

Yu, Hongmei , et al., "Forcing form and function: biomechanical regulation of tumor evolution", Trends in Cell Biology, 21(1), 2011, 47-56.

Yu, Jiashing , et al., "The use of human mesenchymal stem cells encapsulated in RGD modified alginate microspheres in the repair of myocardial infarction in the rat", Biomaterials, 31(27), 2010, 7012-7020.

Zhu, Junmin , et al., "Design properties of hydrogel tissue-engineering scaffolds", Expert Review of Medical Devices, 8(5), 2011, 607-626.

* cited by examiner

FORMULATIONS FOR PANCREATIC ISLET ENCAPSULATION

CROSS-REFERENCE TO RELATED APPLICATIONS

This application is a 35 U.S.C. § 371 national phase entry of PCT Application PCT/US2019/046278, filed Aug. 13, 2019, and published in English on Feb. 20, 2020, as International Publication No. WO 2020/036918, and which claims the benefit of U.S. Provisional Patent Application Ser. No. 62/764,695, filed Aug. 15, 2018, the disclosure of each of which is incorporated by reference herein in its entirety.

BACKGROUND

Glycemic control in diabetes has been shown to delay the onset of, and slow the progression of, associated pathological complications. However, achieving adequate glycemic control using insulin therapy can be difficult. One alternative to insulin therapy is the transplantation of functioning pancreatic islet cells to diabetic subjects, to provide biological insulin replacement. However, transplanted or grafted islet cells encounter immunological rejection, which can limit the clinical usefulness of this method. Microencapsulation of islet cells has been proposed to reduce or avoid immunological rejection of transplanted islet cells. See, e.g., U.S. Pat. No. 6,783,964 to Opara. There remains a need, however, for new ways to facilitate the effective implantation of live encapsulated pancreatic islet cells for the treatment of diabetes.

SUMMARY

Provided herein according to embodiments is a microcapsule comprising: (a) one or more live mammalian pancreatic islet cells; and (b) an alginate composition encapsulating said islet cells, wherein said alginate composition comprises extracellular matrix proteins solubilized or suspended therein.

In some embodiments, the alginate composition is crosslinked. In some embodiments, the alginate composition is crosslinked with $Ca^{++}$ (e.g., about 12.5, 25, 50 or 100 mM $CaCl_2$) or $Sr^{++}$ (e.g., about 12.5, 25, or 50 mM $SrCl_2$).

In some embodiments, the extracellular matrix proteins are pancreatic extracellular matrix proteins. In some embodiments, the extracellular matrix proteins are human extracellular matrix proteins. In some embodiments, the extracellular matrix proteins are present in an amount of from 0.5, 1 or 2 mg per mL to 5, 8, or 10 mg per mL of the alginate composition.

In some embodiments, the alginate composition is coated with poly-L-lysine and/or poly-L-ornithine.

In some embodiments, the cells are human cells.

In some embodiments, the alginate composition has a storage modulus of from about 0.1, 0.5 or 1 to about 4, 5 or 6 kiloPascals.

Also provided is a composition comprising a plurality of microcapsules as taught herein. In some embodiments, the live mammalian pancreatic islet cells are present at a concentration of about $10^3$ to about $10^4$ islet cells per milliliter of the alginate. In some embodiments, the composition further comprises a pharmaceutically acceptable carrier (e.g., endotoxin-free and/or pyrogen-free saline).

Further provided is a method of treating diabetes in a subject in need thereof, comprising administering the composition to said subject in a treatment-effective amount. In some embodiments, the administering comprises transplanting the composition into the peritoneal cavity and/or the omentum of the subject. In some embodiments, the cells and/or ECM are autologous with respect to the subject.

Also provided is a microcapsule or composition as taught herein for use in treating type I diabetes in a subject in need thereof, or in the preparation of a medicament for treating type I diabetes.

DETAILED DESCRIPTION

Figure 1:
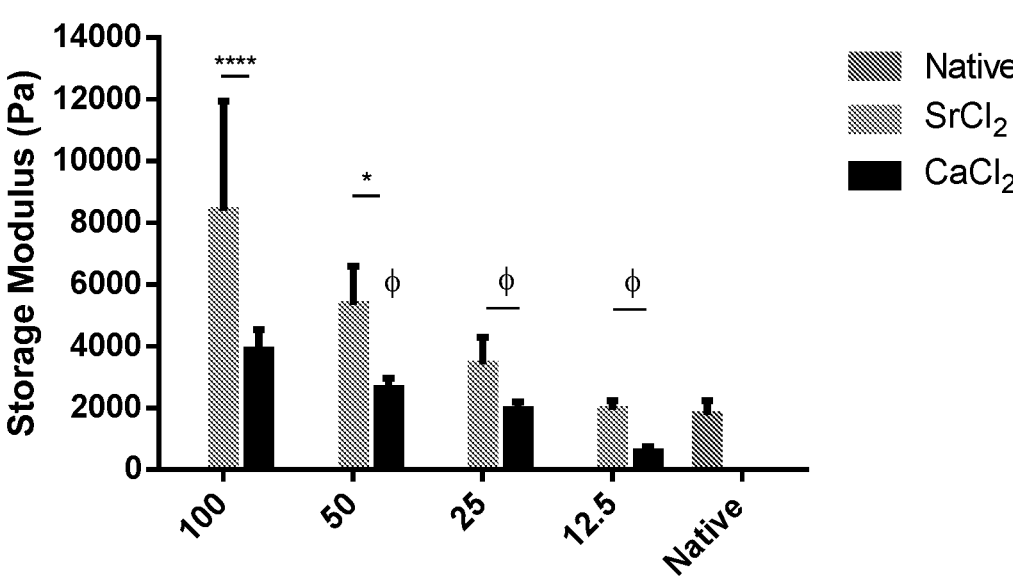
FIG. 1: Storage modulus of alginate hydrogels with either $Sr^{2+}$ or $Ca^{2+}$ crosslinkers ranging from 100 mM to 12.5 mM. Human pancreas tissue (native) also measured for comparisons. Error bars indicate standard deviation, *$=p<0.05$, ****$=p<0.0001$, $\varphi=p>0.05$ compared to native, n=4).

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" or "comprising," when used in this specification, specify the presence of stated features, integers, steps, operations, elements components and/or groups or combinations thereof, but do not preclude the presence or addition of one or more other features, integers, steps, operations, elements, components and/or groups or combinations thereof.

As used herein, the term "and/or" includes any and all possible combinations of one or more of the associated listed items, as well as the lack of combinations when interpreted in the alternative ("or").

Unless otherwise defined, all terms (including technical and scientific terms) used herein have the same meaning as commonly understood by one of ordinary skill in the art to which this invention belongs. It will be further understood that terms, such as those defined in commonly-used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measureable value may include any other range and/or individual value therein.

"Subjects" as used herein are, in general, mammalian subjects. While human subjects are preferred, the subjects may in some embodiments be other animals, such as dogs and cats for veterinary purposes.

"Treat" as used herein refers to any type of treatment that imparts a benefit to a subject, including but not limited to delaying the onset or reducing the severity of at least one symptom in the subject, such as a symptom associated with Type I diabetes.

"Pharmaceutically acceptable" as used herein means that the carrier, microcapsule and/or composition is suitable for administration to a subject to achieve the treatments described herein, without unduly deleterious side effects in light of the severity of the disease and necessity of the treatment.

Live mammalian cells used to carry out the present invention may be collected from a suitable donor. Donors are, in general, mammalian (e.g., human, dog, cat, rabbit, rat, mouse, monkey, chimpanzee, horse, pig, goat, sheep). The donor may be of the same species as the subject being treated, or of a different species. Cells may be isolated from donors and cultured for microcapsule production as desired in accordance with techniques known in the art. In general, fresh tissue may be divided by mincing, teasing, comminution and/or collagenase digestion. The desired cells are then isolated from contaminating cells and materials by washing, filtering, centrifuging or picking procedures, and optionally cultured and/or cryopreserved as desired prior to encapsulation.

Encapsulation of live cells in alginate can be carried out in accordance with known techniques or variations thereof that will be apparent to those skilled in the art. See, e.g., U.S. Pat. Nos. 6,783,964 and 6,365,385 to Opara, the disclosures of which are incorporated by reference herein in their entirety. In some embodiments, the cells are coated with alginate, which is then crosslinked with a divalent cation such as calcium (Ca++) and/or strontium (Sr++). In some embodiments, the crosslinked alginate has a storage modulus of from about 0.1, 0.5 or 1 to about 4, 5 or 6 kiloPascals.

Microcapsules useful in the present invention may optionally have at least one semipermeable membrane surrounding a cell-containing interior. The semipermeable membrane permits the diffusion of nutrients, biologically active molecules and other selected products through the surface membrane and into the microcapsule core. The surface membrane contains pores of a size that determines the molecular weight cut-off of the membrane. The membrane pore size may be chosen to allow the passage of an agent (e.g., insulin) from within the capsule to the external environment, but to exclude the entry of host immune response factors (where the encapsulated cells are not autologous). Such a semipermeable membrane may be formed from a polycation such as a polyamine (e.g., polylysine and/or polyornithine).

In one non-limiting example embodiment of an encapsulation technique, U.S. Pat. No. 4,391,909 to Lim et al describes a method in which cells are suspended in sodium alginate in saline, and droplets containing cells are produced. Droplets of cell-containing alginate flow into calcium chloride in saline. The negatively charged alginate droplets bind calcium and form a calcium alginate gel. The microcapsules are washed in saline and incubated with poly-L-lysine or poly-L-ornithine (or combinations thereof); the positively charged poly-l-lysine and/or poly-L-ornithine displaces calcium ions and binds (ionic) negatively charged alginate, producing an outer poly-electrolyte semipermeable membrane. An exterior coating of sodium alginate may be added by washing the microcapsules with a solution of sodium alginate, which ionically bonds to the poly-L-lysine and/or poly-L-ornithine layer. This may serve to reduce any inflammatory response that may be provoked in the subject by contact of the polycationic membrane to tissue.

Encapsulation may also be performed with a device such as a microfluidic device. See, e.g., Tendulkar et al, "A scalable microfluidic device for the mass production of microencapsulated islets," Transplantation proceedings, Elsevier: 2011; pp 3184-3187; see also U.S. Pat. No. 7,759, 111 to Lee et al., incorporated by reference herein. The microfluidic device may include a plurality of functional regions to shear, focus, and encapsulate a desired cell or group of cells into a droplet. The microfluidic device can further comprise a polymerization zone to form a polymer bead (e.g., alginate) around the droplet.

When desired, the alginate-polylysine microcapsules can be incubated in sodium citrate to solubilize any calcium alginate that has not reacted with poly-L-lysine, i.e., to solubilize the internal core of sodium alginate containing the cells, thus producing a microcapsule with a liquefied cell-containing core portion. See Lim and Sun, Science 210:908 (1980).

Additional non-limiting examples of encapsulation methods for pancreatic islet cells may be found, e.g., in Farney et al., "Review: Evolution of Islet Transplantation for the Last 30 Years," *Pancreas* vol. 45, no. 1, January 2016, pp. 8-20.

In some preferred embodiments, the encapsulating composition comprises extracellular matrix (ECM) proteins, which may be obtained, for example, from a decellularized extracellular matrix composition from a tissue corresponding to the tissue cells (e.g., decellularized extracellular pancreatic matrix). For example, a decellularized pancreas tissue may be lyophilized and ground into a powder to provide extracellular matrix proteins normally found in the pancreas, which may then be combined with a biopolymer (e.g., alginate) to form a hydrogel for encapsulation of the pancreatic islet cells.

In some embodiments, the ECM is from human pancreatic tissue. In some embodiments, the ECM is from the tissue of a patient to be treated (i.e., autologous).

In some embodiments, the ECM is obtained with a decellularization process comprising incubation(s) in deionized water. In some embodiments, the decellularization process comprises an enzymatic digestion (e.g., with DNAse). In some embodiments, the ECM is solubilized (e.g., by incubation with pepsin).

When desired, the microcapsules may be treated or incubated with a physiologically acceptable salt such as sodium sulfate or like agents, in order to increase the durability of the microcapsule, while retaining or not unduly damaging the physiological responsiveness of the cells contained in the microcapsules. See, e.g., U.S. Pat. No. 6,783,964 to Opara.

Microcapsules of the present invention may be administered after production, refrigerated and/or cryopreserved for subsequent use, and/or cultured for subsequent use, as desired. Microcapsules of the invention may be washed (e.g., in sterile physiological saline solution) prior to formulation and/or administration, as needed depending upon their manner of production.

Encapsulated islet cells of the present invention may be administered per se or formulated for administration by any suitable technique, such as by mixing with a pharmaceutically acceptable carrier such as a sterile, endotoxin-free and/or pyrogen-free physiological saline solution. The encapsulated islet cells may be administered by any suitable technique, including but not limited to surgical implantation and/or injection into the pancreas. In some embodiments, administering comprises transplanting the composition into the peritoneal cavity and/or the omentum of the subject.

Dosage of cells administered can be determined in accordance with known techniques or variations thereof that will be apparent to those skilled in the art. For example, in the treatment of diabetes, the International Islet Transplant Registry has recommended transplants of at least 6,000 cells per kilogram of recipient body weight, to achieve euglycemia. In the present invention, the number of cells implanted will depend upon the age and condition of the subject, the particular disorder being treated, etc. In some embodiments of the present invention, from 1,000, 2,000 or 3,000 cells per kilogram of recipient body weight, up to 20,000, 40,000 or 60,000 cells per kilogram recipient body weight, are administered.

Subjects or patients to be treated by the methods and encapsulated islet cells of the present invention include subjects afflicted with Type I diabetes, for which insulin replacement is needed.

The present invention is explained in greater detail in the following non-limiting Examples.

EXAMPLES

Effect of Alginate Matrix Engineered to Mimic the Pancreatic Microenvironment on Encapsulated Islet Function.

Islet encapsulation is a promising strategy with the potential to cure Type 1 Diabetes Mellitus (T1D) due to the proven ability of immune tolerance and suitability in xenotransplantation. See Elliott, Robert B., et al. "Live encapsulated porcine islets from a type 1 diabetic patient 9.5 yrs after xenotransplantation." Xenotransplantation 14.2 (2007): 157-161. This technique has not become clinically translatable though for many reasons. Sustained graft function remains a major challenge for clinical translation of encapsulated islets. Islet encapsulation is performed following successful islet isolation that destroys the natural pancreatic matrix, and inflicts significant damage to the islets. See Farney A C, Sutherland D E R, Opara E C. Evolution of islet transplantation for the last 30 years. Pancreas 45(1):8-20, 2016.

Although current encapsulation techniques that utilize 100 mM $CaCl_2$ for crosslinking alginate hydrogel provide a 3D culture environment for islets, they fail to address critical issues such as the stiffness of the matrix and the necessity for cell adhesion molecules and growth factors that are present in the native pancreatic scaffold in which islets are naturally embedded. We hypothesized that the function of encapsulated islets would be enhanced by tuning the mechanical and biological properties of the alginate to match that of the native pancreas. The purpose of the present study was to examine the effect of an engineered alginate matrix that mimics the native microenvironment of the pancreas on encapsulated islet function in vitro.

Materials and Methods:

Low viscosity (20-200 mPa·s) ultra-pure sodium alginate with high mannuronic acid (LVM) were purchased from Nova-Matrix (Sandvika, Norway). ECM powder was obtained via decellularization of human pancreatic tissue followed by pulverization with a cryo mill. The powder was then solubilized with pepsin and finally mixed with LVM alginate at concentration of 1.5% (w/v) for use in studies. Cell viability was assessed with a 6-carboxyfluorescein diacetate and propidium iodide (CFDA-PI) kit purchased from Invitrogen (Eugene, OR). Insulin response to glucose stimulation was tested with a dynamic perifusion glucose challenge and measured with an Insulin AlphaLISA kit purchased from Perkin Elmer (Waltham, MA).

By adjusting the crosslinker type and concentration, we found that we could modulate the storage modulus of the alginate to match that of a native pancreas. We fabricated alginate hydrogels crosslinked with either Ca++ or Sr++ without or with 2 mg/mL ECM. The ECM incorporated was solubilized into the alginate hydrogel to provide key ECM components such as collagen, laminin, and fibronectin to the islets. We studied four groups of isolated human islets, which were cultured over 48 hours at 37° C. after encapsulation in 1.5% LVM, namely: (1) unencapsulated islets, (2) islets encapsulated in alginate crosslinked with 100 mM $CaCl_2$, (3) islets encapsulated in alginate crosslinked with 25 mM $SrCl_2$, and (4) islets encapsulated in alginate crosslinked with 25 mM $SrCl_2$ and supplemented with solubilized ECM. Assessments of encapsulated isle viability and function were made before and after 2 days following encapsulation. A One-Way ANOVA with Tukey correction statistical procedure was used for data evaluation.

Results:

We found that the alginate hydrogel matrix crosslinked with 25 mM $SrCl_2$ had similar storage modulus as the native pancreatic matrix.

The incorporation of ECM into the 25 mM Sr++-crosslinked alginate resulted in significantly increased rate of both basal and high glucose-stimulated insulin secretion when compared to the other 3 groups. Thus, while basal insulin secretion at 3.3 mM glucose was similar for groups 1-3, the level of basal insulin secretion was higher with the ECM supplementation of the Sr++-crosslinked matrix (p<001, n=4). Also, islets encapsulated in the ECM-supplemented alginate matrix had significantly higher insulin secretion under high glucose (16.7 mM) conditions compared to each of the other experimental groups (p<001).

Conclusion:

We conclude that a fabricated alginate encapsulation matrix can simulate the natural microenvironment of islets in the native pancreas and enhance the function of encapsulated islets.

Materials and Methods

Materials

Unless otherwise noted, all materials and reagents were purchased from Sigma-Aldrich (St. Louis, MO, USA). High-mannuronic acid-low viscosity alginate (LVM) were purchased from Nova-Matrix (Sandvika, Norway) and was reported by the manufacturer to have a molecular weight 75-200 kDa and G/M ratio of ≤1.

Rheological Measurement

The mechanical stiffness of alginate was measured with a Discovery HR-2 hybrid Rheometer (TA Instruments) using a stress-sweep program that calculated the storage modulus of the polymer. This stress-sweep program measured from 0.6 to 10 Pa and a frequency of 1 Hz and a 12 mm parallel plate (TA Instruments). First, alginate discs were made by placing 0.1 mL of 1.5% LVM alginate in a 48 well plate well then adding 0.5 mL of either $CaCl_2$ or $SrCl_2$ crosslinking solution ranging from 100-12.5 mM. The discs were allowed to crosslink for 15 minutes, removed from the well plate, followed by gentle dabbing of a Kim Wipe to remove excess liquid. The hydrogels were then placed under the rheometer and compressed to determine the storage modulus. Human pancreas tissue was cut into a similar shape and measured with the same stress-sweep program in order to determine its storage modulus.

Extracellular Matrix Preparation

Decellularization process: Diced pancreatic tissue was placed in a sterile container with 1000 ml of ultrapure endotoxin free sterile deionized water (10977-015, Invitrogen) and left shaking for 24 hours at 200 rpm at 4° C. After this initial step the tissue underwent an enzymatic digestion with a DNAse (Deoxyribonuclease I from bovine pancreas) in 0.0025% magnesium chloride solution with adjusted pH 7.4 at 37° C. on a shaker at 100 rpm for 6 h. Following the enzymatic digestion the tissue was incubated in an EDTA-Trizma base solution on a shaker at 200 rpm for 18 h at 4° C. In the final step of decellularization the tissue was washed in sterile deionized H2O on a shaker at 200 rpm for 24 h at 4° C. The resultant wet scaffold was frozen at –80° C., lyophilized and cryomilled to obtain a fine ECM powder.

Pancreatic ECM Solubilization: The pancreatic ECM was solubilized according to the method published by Freytes at al. (Biomaterials 2008, 29 (11), 1630-1637): 1 g of ECM was solubilized in 100 ml of 0.01M HCl with 100 mg of pepsin for 48 hours, at room temperature with constant stirring. The pH of the solubilized ECM was re-equilibrated to pH 7.4 with NaOH to irreversibly inactivate the pepsin. The solubilized ECM was centrifuged, the supernatant was collected and frozen at –80° C. and lyophilized. The fine powder, obtained from the lyophilization of the supernatant of the solubilized ECM, now called UltraPure Soluble ECM, was vialed in glass ampoules, sealed and subsequently Gamma irradiated (1.2 Megarad) using the least amount of radiation over 36 hours. Histological analysis of native pancreas and the decellularized pancreas was performed and showed a complete loss of nuclear structure in the decellularized group.

Alginate Preparation

Control alginate solutions were prepared by mixing 1.5% (w/v) with HBSS (H6648, Sigma) and stirring overnight at 4° C. Solubilized ECM was diluted with HBSS at a concentration of 2 mg ECM/mL and used to prepare the ECM-alginate solutions.

Islet Encapsulation and Culture

Human pancreatic islets and pancreatic islet media (PIMS) were purchased from Prodo Laboratories, Inc (Aliso Viejo, CA, USA). Islets were gently mixed with alginate at a concentration of $3\times10^3$ islet/mL alginate. The cell suspension was then pumped through a 2 channel microfluidic device 27 at a flow rate of 0.2 mL/min with an air pressure of 2.0 psi. The microcapsules were collected in either a 100 mM $CaCl_2$ bath with 10 mM HEPES or a 25 mM SrCl2 bath with 10 mM HEPES and allowed to crosslink for 10 minutes prior to washing with HBSS. After washing, microcapsules were placed in PIMS and cultured at 37° C. with 5% $CO_2$ for up to 7 days and analyzed with live/dead assay, static GSIS, and DNA content.

Live/Dead Staining of Islets

Cell viability was assessed using a live/dead stain with CFDA and PI at 1, 4, and 7 days post-encapsulation. Islets were first incubated with 200 μL of 25 μM CFDA in HBSS for 15 minutes. The CFDA was then aspirated and replaced with 200 μL of PIMS and incubated for 30 minutes at 37° C. The PIMS was replaced with a 50 μg/mL solution of PI, and incubated at room temperature for two minutes and then washed with HBSS. The stained islets were imaged under fluorescent light with an Olympus IX71 inverted microscope equipped with standard filters.

Glucose Stimulated Insulin Secretion (GSIS)—Static Assay

In order to determine the biological and mechanical impact of the ECM and crosslinker type and concentration, respectively, on islet functionality, the islets were tested using a static GSIS assay. On days 4 and 7 post-encapsulation, ~150 IEQ per group in triplicates were collected and sequentially incubated with Kreb's buffer containing low (2.8 mM) and high (16.8 mM) glucose concentration followed by KCl depolarization solution (25 mM). The glucose challenge was performed based off a modified protocol previously described (Fraker, C. A., The Role of Oxygen During In Vitro Culture and Immunoisolation of Islets of Langerhans. 2011). Initially, poly prep chromatography tubes (731-1550, Bio-Rad) were filled with Sephadex G-10 beads while free islets or encapsulated islets were located in the middle. Each column was filled with low glucose solution and incubated for one hour as a pre-incubation period for the islets. Next, the pre-incubation medium was replaced with fresh low glucose solution and incubated for one hour for baseline assessment. The solution was then replaced with the high glucose solution for one hour, followed by an additional low glucose phase lasting 1 hour (post-glucose stimulation basal test) followed by a one hour KCl stimulation. The medium from each incubation phase was collected and stored at –80° C. for later analysis. After final media collection, 1 mL of DNA extraction buffer was added to each column and frozen at –20° C. overnight. Finally, the extraction buffer was allowed to thaw, collected, and stored at –80° C. for later DNA quantification. Insulin content was measured with the Perkin Elmer Insulin AlphaLISA (AL204C, Perkin Elmer). DNA content was measured with the Invitrogen picogreen kit (P11496, Invitrogen). The glucose stimulation index (GSI) is calculated as the ratio of insulin release during the high glucose phase to the mean insulin release during the two low glucose incubation phases. This is an effective way to show the responsiveness of the islets based on the glucose concentration.

Results

Rheological Measurement

The storage modulus of alginate hydrogels shown in FIG. 1 indicated that the stiffness of the hydrogel can be directly controlled by varying the crosslinker type and concentration. Calcium crosslinked alginate had a stiffness of 3882.8±652.0 Pa, 2635.0±324.6 Pa, 1938.6±264.3 Pa, and 573.4±165.4 Pa at $CaCl_2$ concentrations of 100 mM, 50 mM, 25 mM, and 12.5 mM respectively. Strontium crosslinked alginate was much stiffer compared to calcium crosslinked alginate at similar concentrations, which is due to the higher binding affinity of the strontium molecule. The stiffness levels at 100 mM, 50 mM, 25 mM, and 12.5 mM $SrCl_2$ were 8377.4±3551.3 Pa, 5353.9±1229.0 Pa, 3408.9±874.6 Pa, and 1927.4±301.8 Pa respectively. At both 100 mM and 50 mM, there were significant differences between calcium and strontium crosslinked alginate hydrogels whereas the margins between them became smaller at 25 mM and 12.5 mM, as shown in FIG. 1.

Figure 2:
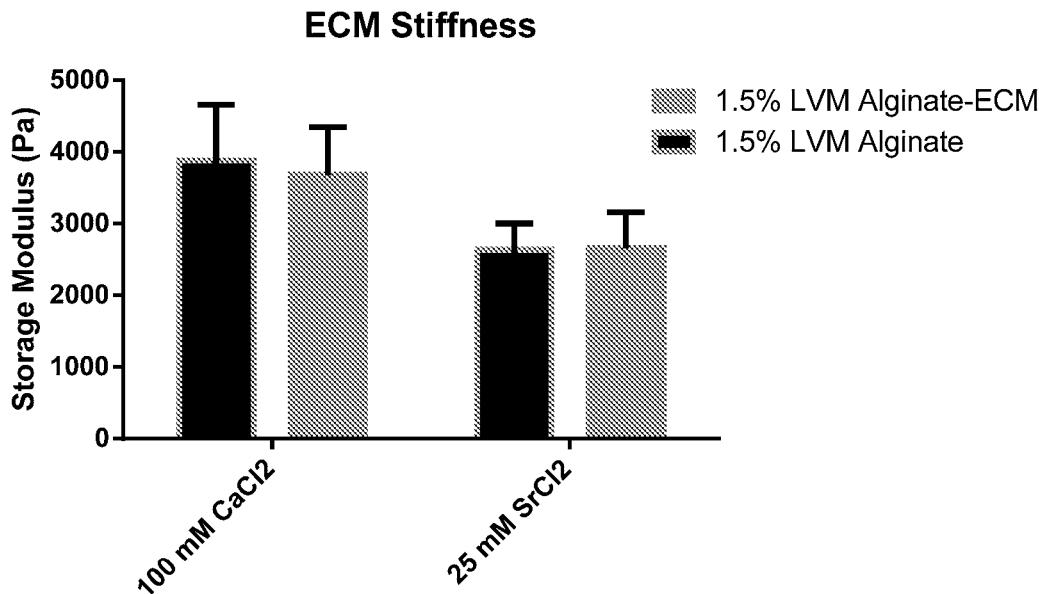
FIG. 2: Storage modulus of alginate±solubilized ECM. No significance was shown within crosslinker concentrations (mean±SD, $p<0.05$, n=4).

When comparing the hydrogels to native pancreas tissue, there were no significant differences to hydrogels made with both crosslinkers at 12.5 mM and 25 mM as well as 50 mM $CaCl_2$. This means that the levels of stiffness obtained with these five different combinations of crosslinker type and concentration closely resemble that of the native human pancreas tissue from a mechanical perspective. Alginate hydrogels with and without ECM were also compared to determine if the addition of solubilized ECM had any impact on the stiffness (FIG. 2). There was no statistically significant difference between groups at similar concentrations in levels of stiffness measured in hydrogels made with both 100 mM and 25 mM $CaCl_2$ with and without ECM.

Islet Viability and Functionality Assessment

Figure 3:
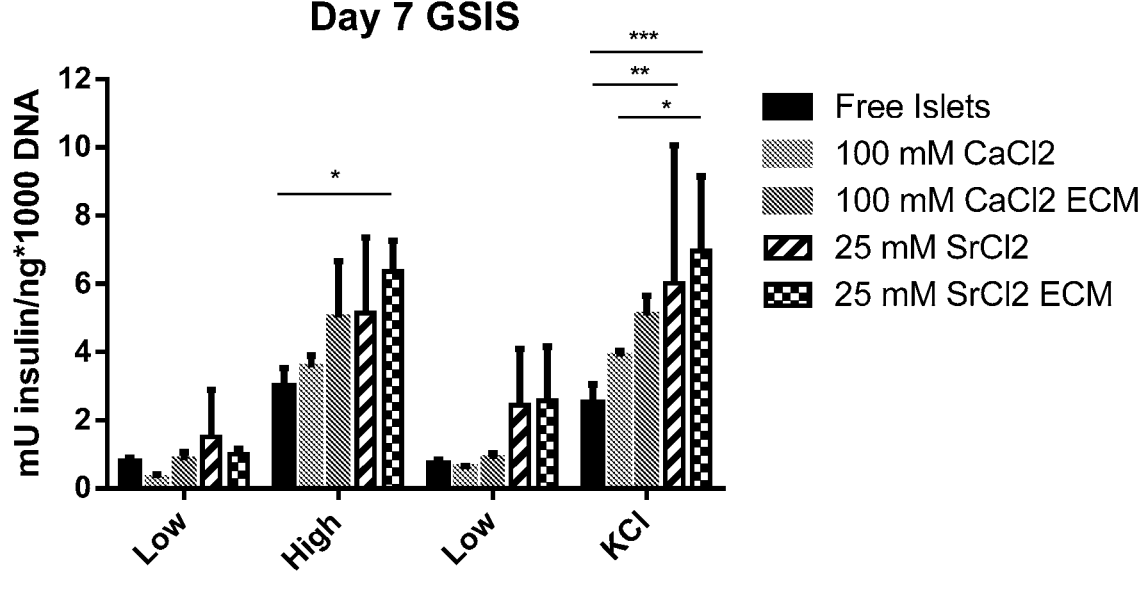
FIG. 3: Islet GSIS results on day 7 post-encapsulation (Mean±SD, *$=p<0.05$, $=p<0.01$, *$=p<0.001$).
Figure 4:
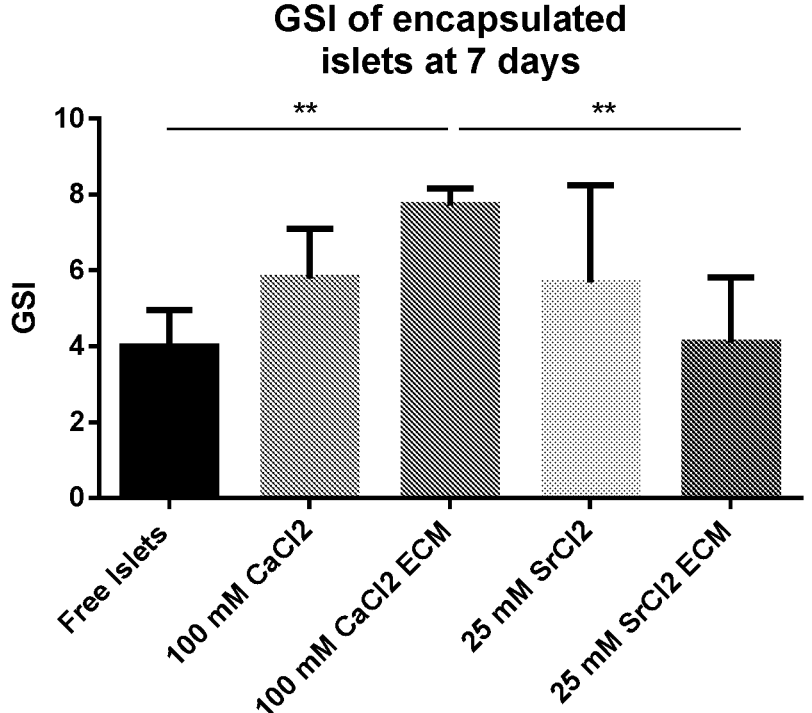
FIG. 4: Glucose stimulation index for both days 4 and 7 post-post encapsulation. Each bar represents the average GSI per group, which is defined as the insulin secretion during the high glucose period divided by the average of the insulin secretion during the low glucose phase. Error bars represent the SD, **$=p<0.01$.

Islet viability stains at 7 days indicate there was a significant increase in viability of cells encapsulated in the softer gels (25 mM $SrCl_2 \pm ECM$) as well as 100 mM $CaCl_2$ with ECM. Unencapsulated islets showed the least number of viable cells with very apparent necrotic cores, while the islets in 100 mM $CaCl_2$-crosslinked hydrogel had cells with slightly more necrotic core. Static GSIS results (FIG. 3) combined with GSI results (FIG. 4) illustrate the functionality of the islets within each group. Islets encapsulated in 25 mM $SrCl_2$ alginate hydrogels with ECM produced $6.37 \pm 0.89$ mU insulin/1000 ng DNA during the high glucose phase, which was significantly more than the amount ($3.00 \pm 0.54$ mU insulin/1000 ng DNA) obtained with unencapsulated islets, n=3, p<0.01). The KCl depolarization phase results indicate that the islets in softer capsules with ECM had significantly more insulin ($6.97 \pm 2.19$ mU insulin/1000 ng DNA) compared to the islets in hard capsules without ECM and unencapsulated islets ($3.89 \pm 0.15$ and $2.51 \pm 0.55$ mU insulin/1000 ng DNA respectively). The islets in soft capsules without each also stored more insulin ($6.02 \pm 4.05$ mU insulin/1000 ng DNA) than the unencapsulated islets (n=3, p<0.05). There was no difference in insulin secretion between both low glucose phases, albeit, both of the softer gels had, on average, higher insulin secretion than the other groups. The GSI results indicate a significant increase in functionality for islets encapsulated in 100 mM $CaCl_2$ alginate with ECM ($7.72 \pm 0.45$) compared to both unencapsulated islets ($4.00 \pm 0.95$) and islets in 25 mM $SrCl_2$ alginate with ECM ($4.10 \pm 1.72$) (average±SD, n=3, p<0.01).

Discussion

The mechanical and biological properties of polymers used for 3D cell culture have been shown to be extremely important towards recreating the physiological conditions of the ECM surrounding those cells. In this report, we modulated the stiffness of our alginate hydrogel to closely resemble that of the human pancreas scaffold in which islets naturally reside. In particular, we have examined Sr++ as an alternative to the more routinely used Ca++ crosslinker for alginate hydrogel driven based on the following observations. First, being our group had observed color changes after about 30 days in vitro incubations of our Ca++-crosslinked hydrogel microcapsules and this was accompanied by a decrease in functionality and viability of the cells encapsulated within them. Indeed, it has been reported that Ca++ can be released from alginate gels and promote inflammatory responses in vitro and in vivo. In addition, it is known that the stiffness of a capsule matrix has profound effect on the behavior of encapsulated stem cells. However, there is scarcity of data on the effect of the matrix stiffness on encapsulated primary cell graft function.

When we switched from calcium to strontium for alginate crosslinking, the change of alginate microbead color over time no longer occurred consistent with possible Ca++ leaching from the Ca++-alginate hydrogel. However, we found that although the stiffness of the 12.5 mM $SrCl_2$-alginate hydrogel was closer to that of the native human pancreas it was too fragile and deemed not durable enough for long-term in vivo encapsulation. Addition of the solubilized ECM to the hydrogel at the specified concentration did not affect the stiffness of the hydrogel. While the major ECM components such as collagen, fibronectin, and elastin impact the biomechanical properties of tissues, it does not appear that their interactions with each other under our experimental conditions are sufficient enough to significantly change the stiffness of our engineered alginate-based matrix. However, our data clearly show that the presence of the solubilized ECM provided some of the many biological signals that influence cell proliferation, differentiation, survival, and tissue specific function. After 7 days incubation, the soft gel containing ECM was the only group that had significantly higher insulin secretion during the high glucose phase compared to the control islet group. Also, the higher insulin secretion demonstrated by KCl stimulation of the soft capsules±ECM groups suggest the storage of more insulin than the standard hydrogel group crosslinked with 100 mM $CaCl_2$ alginate as well as the unencapsulated islet group. Although both of these groups are presently used clinically, our data show that their functionalities are relatively limited compared to the hydrogels crosslinked made with 25 mM $SrCl_2$ in the presence of ECM.

The GSI results generated in this study should be interpreted in conjunction with GSIS data since the lower GSI values for 25 mM $SrCl_2$-alginate with ECM compared to the other groups after 7 days in culture can be explained by the higher basal levels of insulin secretion shown in that group.

Our data consistently show that the incorporation of the ECM into the alginate hydrogel has a profound biochemical impact on the responsiveness of the islets to glucose stimulation. Previous studies have examined the effect of individual ECM proteins, such as collagen, laminin, and RGD, added to alginate hydrogels on islet viability and functionality (Llacua et al. 2016, Lee et al. 2012, Riopel et al., 2014). While this may provide a quicker path through the regulatory process since the protein concentrations are known, there is a plethora of other lesser proteins and molecules that make up the complex microenvironment and provide signals and support to the islets.

We have shown that we can improve both the function and viability of these pancreatic islets by encapsulating them in an engineered alginate matrix that closely mimics the native pancreas ECM both biochemically and biomechanically. Using this engineered matrix to demonstrate improved islet viability and insulin production and, we predict that encapsulated islet transplantation may prove to be more successful in the future with the potential to impact the management of T1DM. In conclusion, the present study has clearly shown that the microenvironment within the matrix in which islets are encapsulated has a profound effect on the viability and function of the islet cells.

REFERENCES

1. Calafiore, R.; Basta, G., Alginate/poly-L-ornithine microcapsules for pancreatic islet cell immunoprotection. In Cell encapsulation technology and therapeutics, Springer: 1999; pp 138-150.
2. De Vos, P.; De Haan, B.; Wolters, G.; Strubbe, J.; Van Schilfgaarde, R., Improved biocompatibility but limited graft survival after purification of alginate for microencapsulation of pancreatic islets. Diabetologia 1997, 40 (3), 262-270.
3. Vaithilingam, V.; Tuch, B. E., Islet transplantation and encapsulation: an update on recent developments. The review of diabetic studies: RDS 2011, 8 (1), 51.

4. Opara, E. C.; McQuilling, J. P.; Farney, A. C., Microencapsulation of Pancreatic Islets for Use in a Bioartificial Pancreas. In Organ Regeneration: Methods and Protocols, Basu, J.; Ludlow, J. W., Eds. Humana Press: Totowa, NJ, 2013; pp 261-266.

5. Jansson, L.; Hellerström, C., Stimulation by glucose of the blood flow to the pancreatic islets of the rat. Diabetologia 1983, 25 (1), 45-50.

6. Lifson, N.; Kramlinger, K. G.; Mayrand, R. R.; Lender, E. J., Blood flow to the rabbit pancreas with special reference to the islets of Langerhans. Gastroenterology 1980, 79 (3), 466-473.

7. Ibarra, V.; Appel, A. A.; Anastasio, M. A.; Opara, E. C.; Brey, E. M., Evaluation of the tissue response to alginate encapsulated islets in an omentum pouch model. Journal of biomedical materials research. Part A 2016, 104 (7), 1581.

8. McQuilling, J.; Arenas-Herrera, J.; Childers, C.; Pareta, R.; Khanna, O.; Jiang, B.; Brey, E.; Farney, A.; Opara, E. In New alginate microcapsule system for angiogenic protein delivery and immunoisolation of islets for transplantation in the rat omentum pouch, Transplantation proceedings, Elsevier: 2011; pp 3262-3264.

9. Darrabie, M. D.; Kendall Jr, W. F.; Opara, E. C., Characteristics of poly-L-ornithine-coated alginate microcapsules. Biomaterials 2005, 26 (34), 6846-6852.

10. Darrabie, M. D.; Kendall, W. F.; Opara, E. C., Effect of alginate composition and gelling cation on micro-bead swelling. Journal of microencapsulation 2006, 23 (1), 29-37.

11. de Vos, P.; Faas, M. M.; Strand, B.; Calafiore, R., Alginate-based microcapsules for immunoisolation of pancreatic islets. Biomaterials 2006, 27 (32), 5603-5617.

12. Pathak, A.; Kumar, S., Independent regulation of tumor cell migration by matrix stiffness and confinement. Proceedings of the National Academy of Sciences 2012, 109 (26), 10334-10339.

13. Evans, N. D.; Minelli, C.; Gentleman, E.; LaPointe, V.; Patankar, S. N.; Kallivretaki, M.; Chen, X.; Roberts, C. J.; Stevens, M. M., Substrate stiffness affects early differentiation events in embryonic stem cells. Eur cell mater 2009, 18 (1), e13.

14. Discher, D. E.; Janmey, P.; Wang, Y.-l., Tissue cells feel and respond to the stiffness of their substrate. Science 2005, 310 (5751), 1139-1143.

15. Engler, A. J.; Sen, S.; Sweeney, H. L.; Discher, D. E., Matrix Elasticity Directs Stem Cell Lineage Specification. Cell 2006, 126 (4), 677-689.

16. Gilbert, P. M.; Havenstrite, K. L.; Magnusson, K. E.; Sacco, A.; Leonardi, N. A.; Kraft, P.; Nguyen, N. K.; Thrun, S.; Lutolf, M. P.; Blau, H. M., Substrate elasticity regulates skeletal muscle stem cell self-renewal in culture. Science 2010, 329 (5995), 1078-1081.

17. Lopez, J.; Mouw, J.; Weaver, V., Biomechanical regulation of cell orientation and fate. Oncogene 2008, 27 (55), 6981.

18. Frantz, C.; Stewart, K. M.; Weaver, V. M., The extracellular matrix at a glance. J Cell Sci 2010, 123 (24), 4195-4200.

19. Yu, H.; Mouw, J. K.; Weaver, V. M., Forcing form and function: biomechanical regulation of tumor evolution. Trends in cell biology 2011, 21 (1), 47-56.

20. Alberts, B.; Johnson, A.; Lewis, J.; Raff, M.; Roberts, K.; Walter, P., The extracellular matrix of animals. 2002.

21. Llacua, A.; de Haan, B. J.; Smink, S. A.; de Vos, P., Extracellular matrix components supporting human islet function in alginate-based immunoprotective microcapsules for treatment of diabetes. Journal of biomedical materials research Part A 2016, 104 (7), 1788-1796.

22. Hunt, N. C.; Hallam, D.; Karimi, A.; Mellough, C. B.; Chen, J.; Steel, D. H.; Lako, M., 3D culture of human pluripotent stem cells in RGD-alginate hydrogel improves retinal tissue development. Acta biomaterialia 2017, 49, 329-343.

23. Rowley, J. A.; Mooney, D. J., Alginate type and RGD density control myoblast phenotype. Journal of Biomedical Materials Research: An Official Journal of The Society for Biomaterials, The Japanese Society for Biomaterials, and The Australian Society for Biomaterials and the Korean Society for Biomaterials 2002, 60 (2), 217-223.

24. Maia, F. R.; Lourenco, A. H.; Granja, P. L.; Goncalves, R. M.; Barrias, C. C., Effect of cell density on mesenchymal stem cells aggregation in RGD-alginate 3D matrices under osteoinductive conditions. Macromolecular bioscience 2014, 14 (6), 759-771.

25. Yu, J.; Du, K. T.; Fang, Q.; Gu, Y.; Mihardja, S. S.; Sievers, R. E.; Wu, J. C.; Lee, R. J., The use of human mesenchymal stem cells encapsulated in RGD modified alginate microspheres in the repair of myocardial infarction in the rat. Biomaterials 2010, 31 (27), 7012-7020.

26. Freytes, D. O.; Martin, J.; Velankar, S. S.; Lee, A. S.; Badylak, S. F., Preparation and rheological characterization of a gel form of the porcine urinary bladder matrix. Biomaterials 2008, 29 (11), 1630-1637.

27. Tendulkar, S.; McQuilling, J.; Childers, C.; Pareta, R.; Opara, E.; Ramasubramanian, M. In A scalable microfluidic device for the mass production of microencapsulated islets, Transplantation proceedings, Elsevier: 2011; pp 3184-3187.

28. Fraker, C. A., The Role of Oxygen During In Vitro Culture and Immunoisolation of Islets of Langerhans. 2011.

29. Jiang, K.; Chaimov, D.; Patel, S. N.; Liang, J. P.; Wiggins, S. C.; Samojlik, M. M.; Rubiano, A.; Simmons, C. S.; Stabler, C. L., 3-D physiomimetic extracellular matrix hydrogels provide a supportive microenvironment for rodent and human islet culture. Biomaterials 2018.

30. Augst, A. D.; Kong, H. J.; Mooney, D. J., Alginate hydrogels as biomaterials. Macromolecular bioscience 2006, 6 (8), 623-633.

31. Rowley, J. A.; Madlambayan, G.; Mooney, D. J., Alginate hydrogels as synthetic extracellular matrix materials. Biomaterials 1999, 20 (1), 45-53.

32. Nicodemus, G. D.; Bryant, S. J., Cell encapsulation in biodegradable hydrogels for tissue engineering applications. Tissue Engineering Part B: Reviews 2008, 14 (2), 149-165.

33. Barralet, J.; Wang, L.; Lawson, M.; Triffitt, J.; Cooper, P.; Shelton, R., Comparison of bone marrow cell growth on 2D and 3D alginate hydrogels. Journal of materials science: materials in medicine 2005, 16 (6), 515-519.

34. Zhu, J.; Marchant, R. E., Design properties of hydrogel tissue-engineering scaffolds. Expert review of medical devices 2011, 8 (5), 607-626.

35. Skardal, A.; Devarasetty, M.; Kang, H.-W.; Mead, I.; Bishop, C.; Shupe, T.; Lee, S. J.; Jackson, J.; Yoo, J.; Soker, S., A hydrogel bioink toolkit for mimicking native tissue biochemical and mechanical properties in bioprinted tissue constructs. Acta biomaterialia 2015, 25, 24-34.

36. Ho, S. S.; Murphy, K. C.; Binder, B. Y.; Vissers, C. B.; Leach, J. K., Increased survival and function of mesenchymal stem cell spheroids entrapped in instructive alginate hydrogels. Stem cells translational medicine 2016, 5 (6), 773-781.

37. Gasperini, L.; Mano, J. F.; Reis, R. L., Natural polymers for the microencapsulation of cells. Journal of The Royal Society Interface 2014, 11 (100).

38. Badylak, S. F.; Freytes, D. O.; Gilbert, T. W., Extracellular matrix as a biological scaffold material: structure and function. Acta biomaterialia 2009, 5 (1), 1-13.

39. Saldin, L. T.; Cramer, M. C.; Velankar, S. S.; White, L. J.; Badylak, S. F., Extracellular matrix hydrogels from decellularized tissues: structure and function. Acta biomaterialia 2017, 49, 1-15.

40. Lee, B. R.; Hwang, J. W.; Choi, Y. Y.; Wong, S. F.; Hwang, Y. H.; Lee, D. Y.; Lee, S.-H., In situ formation and collagen-alginate composite encapsulation of pancreatic islet spheroids. Biomaterials 2012, 33 (3), 837-845.

41. Riopel, M.; Wang, R., Collagen matrix support of pancreatic islet survival and function. Front Biosci 2014, 19 (1), 77-90.

The foregoing is illustrative of the present invention, and is not to be construed as limiting thereof. The invention is defined by the following claims, with equivalents of the claims to be included therein.

That which is claimed is:

1. A microcapsule comprising:
(a) one or more live mammalian pancreatic islet cells; and
(b) an alginate composition encapsulating said islet cells,
wherein said alginate composition comprises extracellular matrix proteins solubilized therein,
wherein said extracellular matrix proteins are pancreatic extracellular matrix proteins obtained from a decellularized extracellular pancreatic matrix,
wherein said extracellular matrix proteins are present in an amount of from 0.5 mg per mL to 10 mg per mL of the alginate composition,
wherein said alginate composition is a high-mannuronic acid (high-M) alginate composition,
wherein said alginate composition is crosslinked with Sr$^{++}$, and wherein said alginate composition has a storage modulus of from about 0.1 to about 6 kiloPascals.

2. The microcapsule of claim 1, wherein said extracellular matrix proteins are human extracellular matrix proteins.

3. The microcapsule of claim 1, wherein said alginate composition is coated with poly-L-lysine and/or poly-L-ornithine.

4. The microcapsule of claim 1, wherein said cells are human cells.

5. A composition comprising a plurality of microcapsules of claim 1.

6. The composition of claim 5, wherein the live mammalian pancreatic islet cells are present at a concentration of about 10$^3$ to about 10$^4$ islet cells per milliliter of the alginate composition.

7. The composition of claim 5, further comprising a pharmaceutically acceptable carrier.

8. A method of treating diabetes in a subject in need thereof, comprising administering the composition of claim 5 to said subject in a treatment-effective amount.

9. The method of claim 8, wherein said administering comprises transplanting the composition into the peritoneal cavity and/or the omentum of the subject.

10. The method of claim 8, wherein the cells and/or extracellular matrix proteins are autologous with respect to the subject.

11. The microcapsule of claim 1, wherein said Sr$^{++}$ is provided in the form of about 12.5, 25, or 50 mM SrCl$_2$.

12. The composition of claim 7, wherein the pharmaceutically acceptable carrier is endotoxin-free and/or pyrogen-free saline.

13. The microcapsule of claim 1, wherein said alginate composition has a storage modulus of from about 1 to about 4 kiloPascals.

14. The microcapsule of claim 1, wherein said Sr$^{++}$ is provided in the form of about 25 mM SrCl$_2$.

15. The microcapsule of claim 1, wherein said cells are pig cells.

\* \* \* \* \*